United States Patent [19]
Eby, III

[11] Patent Number: 4,503,070
[45] Date of Patent: Mar. 5, 1985

[54] METHOD FOR REDUCING THE DURATION OF THE COMMON COLD

[76] Inventor: George A. Eby, III, 2109 Paramount St., Austin, Tex. 78704

[21] Appl. No.: 378,479

[22] Filed: May 14, 1982

Related U.S. Application Data

[63] Continuation-in-part of Ser. No. 288,750, Jul. 31, 1981, abandoned.

[51] Int. Cl.³ .......................................... A61K 31/315
[52] U.S. Cl. .................................................. 514/494
[58] Field of Search ............................... 424/289, 145

[56] References Cited

PUBLICATIONS

Christison, *A Dispensatory*, Philadelphia; Lee and Blanchard, 1948, p. 983.

Merck Index, 9th ed., Merck and Co., Inc., 1976, p. 1310.

Carter et al., *Chemotherapy of Cancer*, 2nd ed., John Wiley & Sons, pp. 26–29.

Gutman, *Modern Drug Encyclopedia*, 1941, p. 731.

*Primary Examiner*—Delbert R. Phillips
*Assistant Examiner*—F. T. Moezie

[57] ABSTRACT

The invention disclosed and claimed is a method to reduce duration of common colds in humans as evinced by reduction of duration of 10 common cold symptoms through use of zinc gluconate topically and frequently applied to the oral mucosa. The invention improves upon the prior art using zinc intranasally as an astringent and decongestant in treatment of common colds. Results of a clinical study are presented in support of disclosure and claims.

3 Claims, No Drawings

METHOD FOR REDUCING THE DURATION OF THE COMMON COLD

A continuation-in-part of "A Rapid Acting Treatment for the Common Cold" Ser. No. 288,750 filed 7/31/81, now abandoned.

FIELD OF INVENTION

This invention relates to a method for reducing the duration of the common cold in humans.

BACKGROUND

The art of managing viral upper respiratory infections commonly called common colds has not been adequate. Common colds are the most common acute illness in the United States and account for about one-half of all lost school days and lost work days. An estimated one billion colds occur in the United States each year. Thus, there can be no question as to the need for a safe, simple, inexpensive, effective and available treatment to minimize or eliminate this important and costly public health problem.

Heretofore, treatment of common colds involved use of symptomatic therapy. Such therapy did not reduce duration of common colds. For example, with or without treatment, duration of 50% of the common colds caused by rhinoviruses remained at 7 days. Primary common colds symptoms are nasal drainage and nasal congestion. Secondary symptoms often accompanying primary symptoms include: headache, fever, myalgia, sneezing, sore throat, scratchy throat, cough and hoarseness. The prior art teaches individual treatment of each symptom as needed to ameliorate symptoms during their association with a common cold, rather than teaches treatment of the common cold to reduce the duration of all symptoms associated with them.

PRIOR ART

It has been established in vitro that zinc ions can inhibit replication of a few of the many antigenically different rhinoviruses. The concentration of zinc ions required to be antirhinoviral is $10^{-4}$M or greater which is 10 times or greater than the zinc ionic concentration found in human serum. But other in vitro studies have demonstrated that inhibitory effects of zinc on rhinoviruses are reversible and provide no lasting effect once the zinc ions are removed from the medium. According to the latter studies, when zinc is removed from rhinoviruses, they resume their replication and again become fully infective. The best use fo zinc in activities involving the rhinoviruses was suggested to be as a method to temporarily or reversibly inhibit rhinovirus replication in laboratory experiments. Since the antirhinoviral effect was observed to be reversible and since the inhibitory effects had been demonstrated in only a few of the antigenically different viruses known to cause the common cold, zinc was not considered to be a suitable antirhinoviral agent for the treatment of the common cold in humans.

It has been established that zinc can provide an astringent and decongestant effect in common cold treatment. Zinc inhibits the release of histamine from mast cells and basophils. Histamine is a mediator of two primary common cold symptoms. The effect of zinc in inhibiting the release of histamine from mast cells and basophils produces a reduction in histamine mediated nasal drainage and nasal congestion, which might be considered as astringent-like and decongestant. A technique used earlier in this century to provide astringent and decongestant effects in the treatment of common colds requires that 4 to 10 drops of a 0.2% to 2.0% zinc borate aqueous suspension be applied by spray, instillation or Dowling packing into each nostril or eye several times per day. Such an intranasal method operates only to relieve the treated human from certain discomfort associated with the congestion symptoms. But it can now be disclosed that the low dosages of zinc and the method of application only brings temporary relief, perhaps because natural circulation removes zinc ions from the locus of the treatment more rapidly than the low application rate of zinc ions by the dosages replaces them. Because it has been established in vitro that zinc ions can inhibit replication of rhinoviruses, one may theorize that a low dosage of zinc may produce a zinc ion concentration that may or may not reach antiviral concentrations and that a method of application that does not maintain a sufficiently high level of zinc ions in the locus of treatment would not prevent continued viral replication. Regardless of a theoretical justification for a method of decreasing zinc ion concentration, the astringent-like and decongestant effects of the low zinc dosages under the prior art methods of application cease when the treatment is discontinued before the cold has run its normal, untreated duration.

OBJECTIVE OF INVENTION

Accordingly, the objective of this invention is to correct deficiencies of the prior art in treatment of common colds through use of a method that significantly reduces duration of common colds in humans.

SUMMARY OF INVENTION

This invention relates to a new treatment that shortens duration of common colds through use of zinc compounds applied in a manner and at a frequency so as to cause a sustained, above normal concentration of zinc ions in the virally infected tissues until no common cold symptoms remain and without relapse of any common cold symptom.

DETAILED DESCRIPTION OF INVENTION

The invention disclosed and claimed is a method to reduce duration of common colds in humans as evinced by reduction of duration of 10 common cold symptoms defined as being: nasal drainage, nasal obstruction, headache, fever, myalgia, sneezing, sore throat, scratchy throat, cough and hoarseness with each symptom, when present, being a result of a viral upper respiratory infection. Such method involves administration of pharmaceutically acceptable zinc compounds topically applied to oral, pharyngeal and/or nasal mucosal membranes by a manner that raises the concentration of zinc ions in virally infected areas. Those concentrations are maintained for a period of time until all common cold symptoms are eliminated without release. Means of application include, but are not limited to the following direct, indirect, carrier, and special means or any combination of means. Direct application of zinc compounds may be by nasal sprays, nasal drops, nasal ointments, nasal washes, nasal injections, packings, or indirectly through use of throat troches or lozenges, or through use of mouth washes or gargles, or through the use of inhalants or ointments applied to the nasal nares, the bridge of the nose, or the face or any combination of these and similar methods of application. Carriers such as dimethyl sulfoxide and other special methods such as oral ingestion or parenteral introduction of zinc compounds where such treatment allows elevation of zinc ionic concentration in virally infected areas may be used as needed and given by any means of administration. The forms in which the zinc compounds may be administered include but are not limited to lozenges, troches, candies, injectants, chewing gums, tablets, powders, sprays, liquids, ointments, and aerosols. Pharmaceutically acceptable zinc compounds in dosages from 2 to 200 milligrams of zinc include but are not limited to zinc gluconate, zinc ascorbate, zinc citrate, zinc oxide, zinc acetate, zinc picolinate, zinc transferrin, zinc orotate and zinc aspartate.

AN OPERATIONAL METHOD TO DEMONSTRATE INVENTION

The following Treatment Instructions, prepared by the applicant, represent one way of using zinc compounds to reduce duration of common colds. The instructions were used in a random, double-blind, clinically controlled study in the office of Dr. William W. Halcomb, M. D., D. O. during the autumn of 1981 in Austin, Tex. Each tablet used in the double-blind study contained either 23 milligrams of zinc from zinc gluconate or 50 milligrams of calcium lactate as the placebo.

TREATMENT INSTRUCTIONS

At the office visit, patients are each given a bottle of tablets to use to treat the common cold. The patient dissolves the first tablet in the mouth so as to saturate the oral mucosa (lining of the mouth, tongue and throat) and then a second tablet immediately thereafter. Continue treatment after leaving the office during wakeful hours by dissolving in the mouth the appropriate number of tablets following the treatment schedule for age group of patient:

| Age Group | Tablets/ Treatment | Schedule for Treatment | Maximum Daily Dosage |
|---|---|---|---|
| Adult | 1 | Each 2 hours | 12 tablets |
| Youth | 1 | Each 2 hours | 9 tablets |
| Child | ½ | Each 2 hours | 6 tablets |

Patients should not wash down medication with either food, drink or mouthwashes. Patients should be treated immediately prior to bedtime and during the night when awake. After all symptoms have been absent for six hours, the patient may stop treatment.

RESULTS OF STUDY USING TREATMENT INSTRUCTIONS TO DEMONSTRATE INVENTION SO DESCRIBED

Data collected during the study indicate that the group treated with zinc gluconate lozenges recovered faster than did the group treated with placebo. The placebo-treated group responded at a rate identical to untreated rhinovirus common cold patients described in medical literature. The following paragraph is the abstract from a manuscript entitled "Reduction in Duration of Common Colds by Zinc Gluconate Lozenges in a Double-Blind Study" which was prepared from data obtained during the study and was published in Antimicrobial Agents and Chemotherapy, volume 25, pages 20-24, 1984.

As a possible treatment for common colds, we tested zinc gluconate lozenges in a double-blind, placebo-controlled, clinical trial. One 23-mg zinc lozenge or matched placebo was dissolved in the mouth every 2 wakeful hours after an initial double dose. After 7 days, 86% of 37 zinc-treated subjects were asymptomatic, compared with only 46% of 28 placebo-treated subjects (P=0.0005). Side effects or complaints were usually minor and consisted mainly of objectionable taste and mouth irritation. Zinc lozenges shortened the average duration of common colds by about 7 days.

Not only was duration of common colds treated with zinc significantly shorter, but duration of 10 common cold symptoms was shorter and severity of symptoms was also reduced. Duration of common colds is defined as the longest period of time in which any one, or more, of the 10 common cold symptoms remained.

CONTRAINDICATIONS TO TREATMENT

There are no known contraindications to the treatment.

What is claimed is:

1. The method of administering an agent to reduce duration of common cold symptoms in humans, which includes reducing the duration of nasal drainage, nasal congestion, headache, fever, myalgia, sneeezing, sore throat, scratchy throat, cough, and horseness when such symptoms evince existence of a common cold, comprising:

applying, in the form of a lozenge, zinc gluconate to the oral mucosa of a human in need of treatment;

permitting zinc to remain in contact with the mucosa for a period of time necessary for lozenges to dissolve;

and applying additional dosages of zinc until the symptoms have disappeared.

2. The method according to claim 1 wherein dosages of zinc gluconate each contain 2 to 50 milligrams of zinc.

3. The method according to claim 1 wherein the first dosage of zinc gluconate is double that of additional dosages, additional dosages each consists of a single lozenge given two hours after a previously applied dosage, and all dosages are applied during the waking hours of the human in need of treatment.

* * * * *